United States Patent
Hanswillemenke et al.

(10) Patent No.: US 9,274,035 B2
(45) Date of Patent: Mar. 1, 2016

(54) CLAMPING DEVICE

(71) Applicants: Eva Hanswillemenke, Hoxter (DE); Michael Ott, Mülheim an der Ruhr (DE)

(72) Inventors: Hans Hanswillemenke, Höxter (DE); Michael Ott, Mülheim an der Ruhr (DE)

(73) Assignee: SIEMENS AKTIENGESELLSCHAFT, München (KR)

( * ) Notice: Subject to any disclaimer, the term of this patent is extended or adjusted under 35 U.S.C. 154(b) by 160 days.

(21) Appl. No.: 13/746,367

(22) Filed: Jan. 22, 2013

(65) Prior Publication Data
US 2013/0199304 A1    Aug. 8, 2013

(30) Foreign Application Priority Data

Jan. 23, 2012    (DE) .......................... 10 2012 200911

(51) Int. Cl.
*G01N 3/08*    (2006.01)
*G01N 3/02*    (2006.01)
*G01N 3/04*    (2006.01)

(52) U.S. Cl.
CPC .. *G01N 3/02* (2013.01); *G01N 3/04* (2013.01); *G01N 2203/0282* (2013.01)

(58) Field of Classification Search
USPC ......................................................... 73/818
See application file for complete search history.

(56) References Cited

U.S. PATENT DOCUMENTS

| | | | | |
|---|---|---|---|---|
| 4,393,718 A * | 7/1983 | Gebhard et al. | ................. | 73/859 |
| 4,850,231 A * | 7/1989 | Ralfs et al. | ...................... | 73/859 |
| 5,199,304 A * | 4/1993 | Ferguson | ........................ | 73/800 |
| 5,388,018 A * | 2/1995 | Falk | ........................... | 360/271.1 |
| 5,481,086 A * | 1/1996 | Ferguson | ...................... | 219/385 |
| 7,363,822 B2 * | 4/2008 | Lindeman | ...................... | 73/818 |

FOREIGN PATENT DOCUMENTS

| | | | |
|---|---|---|---|
| DE | 3046094 A1 | | 6/1982 |
| DE | 229216 A1 | | 10/1985 |
| DE | 19840422 | * | 3/2000 |
| DE | 19840422 A1 | | 3/2000 |

* cited by examiner

*Primary Examiner* — Lisa Caputo
*Assistant Examiner* — Octavia Hollington (57) ABSTRACT

A clamping device for clamping a flat material test sample while a material test is carried out is provided. The clamping device includes a substantially cylindrical clamping part, from the free end of which there extends a receiving slot for receiving the material test sample, a pressure ring surrounding the clamping part in the region of the receiving slot, and a pressure sleeve provided between the clamping part and the pressure ring, the pressure sleeve is formed and actuable such that, under radial expansion, it connects the clamping part and the pressure ring together and clamps the material test sample held in the receiving slot.

11 Claims, 10 Drawing Sheets

CLAMPING DEVICE

CROSS REFERENCE TO RELATED APPLICATIONS

This application claims priority of German application No. 102012200911.6 DE filed Jan. 23, 2012. All of the applications are incorporated by reference herein in their entirety.

FIELD OF INVENTION

A clamping device for clamping a flat material test sample while a material test is carried out is provided. Also provided is a material testing machine having two such clamping devices.

BACKGROUND OF INVENTION

In order to determine material characteristics which represent the behavior of materials under the influence of external forces, it is well known to subject material test samples prepared from the corresponding material to standardized material tests. One example of such a material test is what is known as the tensile test, by way of which the tensile strength and further material characteristics of a material can be determined. In such material tests, a flat material test sample comprising a rectangular test cutting and a flat sample head is clamped on both sides into a material testing machine using a clamping device, whereupon a load is exerted on the material test sample via the clamping devices. Currently known clamping devices normally operate on the pincer principle, in which the end of the material test sample is gripped or clamped in a pincer-like manner by the clamping device. Such clamping devices have proven successful in particular in the modeling of unidirectional tensile deformations, as occur in particular during the tensile test. However, they reach physical limits when symmetrical alternating tensile and compressive loading is intended to take place, i.e. R=−1, in which case:

$$R = F_{min}/F_{max} = \sigma_{min}/\sigma_{max}$$

where $F_{min}$ is the compressive force with a negative sign and $F_{max}$ is the tensile force with a positive sign. In such alternating tensile and compressive loading, a jump function frequently occurs at the transition from the tensile loading to the compressive loading, because the material test sample begins to slip since the clamping action of the clamping devices that operate according to the pincer principle is insufficient.

Currently, this problem is solved in that symmetrical loading is dispensed with. The material test is thus run in what is known as the range of pulsating tensile stresses where R=0. This means that the tensile force fluctuates, with the minimum stress being 0. Accordingly, the material test sample is not exposed to any compressive force, and so slipping of the material test sample is prevented.

SUMMARY OF INVENTION

Proceeding from this prior art, it is an object to provide a clamping device and a material testing machine of the type mentioned at the beginning with an alternative structure.

In order to achieve this object, a clamping device of the type mentioned at the beginning is provided, comprising a substantially cylindrical clamping part, from the free end of which there extends a receiving slot for receiving the material test sample, a pressure ring surrounding the clamping part in the region of the receiving slot, and a pressure sleeve provided between the clamping part and the pressure ring, said pressure sleeve being formed and actuable such that, under radial expansion, it connects the clamping part and the pressure ring together and nonpositively clamps the material test sample held in the receiving slot. The clamping device is distinguished in particular in that it exerts a uniformly high surface pressure on the material test sample to be clamped, said surface pressure reliably preventing slipping of the material test sample even in the event of alternating loading. Furthermore, the material test sample is centered automatically during clamping, thereby ensuring constant test conditions.

According to one configuration, the receiving slot is widened at the slot base, wherein the widening has a circular cross section.

Such a widening is advantageous to the extent that the receiving slot of the clamping part can be narrowed more easily when the pressure sleeve is actuated, thereby making it easier to clamp the material test sample received in the receiving slot.

The outside diameter of the clamping part has at least one groove in the region of the slot base of the receiving slot, in particular two mutually opposite grooves which are arranged at the same distance from the receiving slot. By way of these grooves, the cross section of the clamping part is selectively weakened, as a result of which it is likewise easier to narrow the receiving slot upon actuation of the clamping sleeve and thus clamp the material test sample received in the receiving slot.

Advantageously, the clamping part has at its other free end a fastening section for arranging the clamping part on a material testing machine. Accordingly, the clamping part can be fastened in a simple manner to a material testing machine or to a test frame of such a material testing machine.

According to one configuration, the fastening section of the clamping part is provided with a thread which can be brought into engagement with a correspondingly formed mating thread on the material testing machine. Accordingly, the clamping part can be screwed easily to the material testing machine.

The pressure ring is in the form of a solid component. The annular structure of the pressure ring thus has in this variant no cavities which weaken the cross section of the pressure ring. Accordingly, the pressure ring absorbs the forces exerted on the clamping part during the clamping operation of the latter with minimum deformation.

According to one configuration, there is provided a cooling collar through which a cooling fluid can flow and which surrounds the pressure ring. Such a cooling collar is intended to prevent disadvantageous effects of high temperatures on the clamping device, in particular a loss or drop in the clamping force or clamping tension.

Advantageously, at least one thermal insulator is provided on an end side of the clamping device, said thermal insulator preferably being formed in a plate-like manner and/or being produced from ceramic material. Such a thermal insulator insulates the clamping device from the effects of high external temperatures. In addition, the action of the cooling collar, when one is provided, is supported.

In order to achieve the object mentioned at the beginning, a material testing machine having two clamping devices of the above-described kind is also provided, which are arranged opposite one another such that the free ends of a flat material test sample is receivable in their receiving slots and the material test sample can be clamped.

BRIEF DESCRIPTION OF THE DRAWINGS

Further features and advantages will become clear from the following description of an embodiment of a clamping device with reference to the accompanying drawing, in which.

DETAILED DESCRIPTION OF INVENTION

Figure 1:
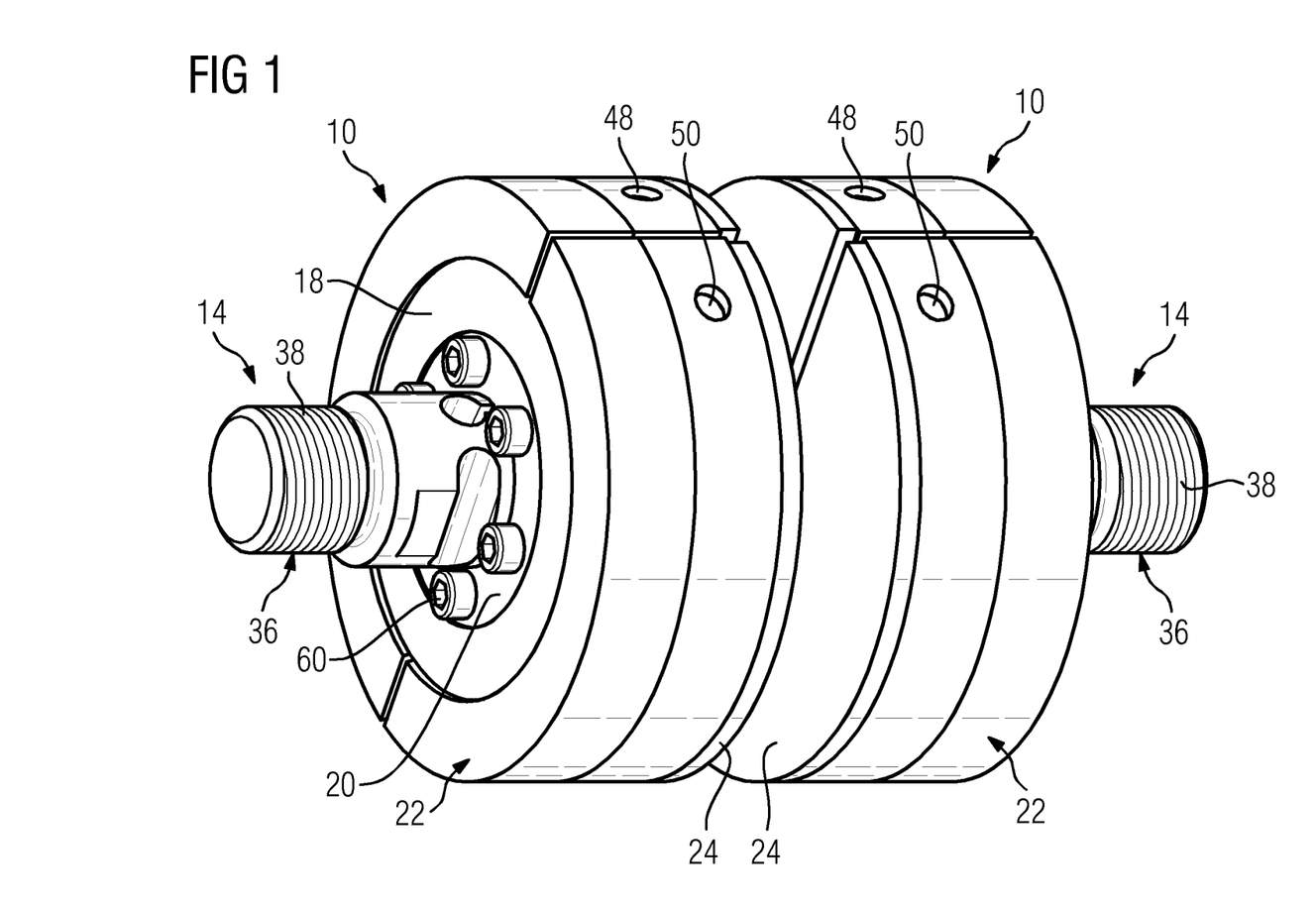
FIG. 1 is a perspective view of two mutually opposite clamping devices according to one embodiment of the present invention, said clamping devices forming a part of a material testing machine according to the invention and a flat material test sample being clamped between them.
Figure 2:
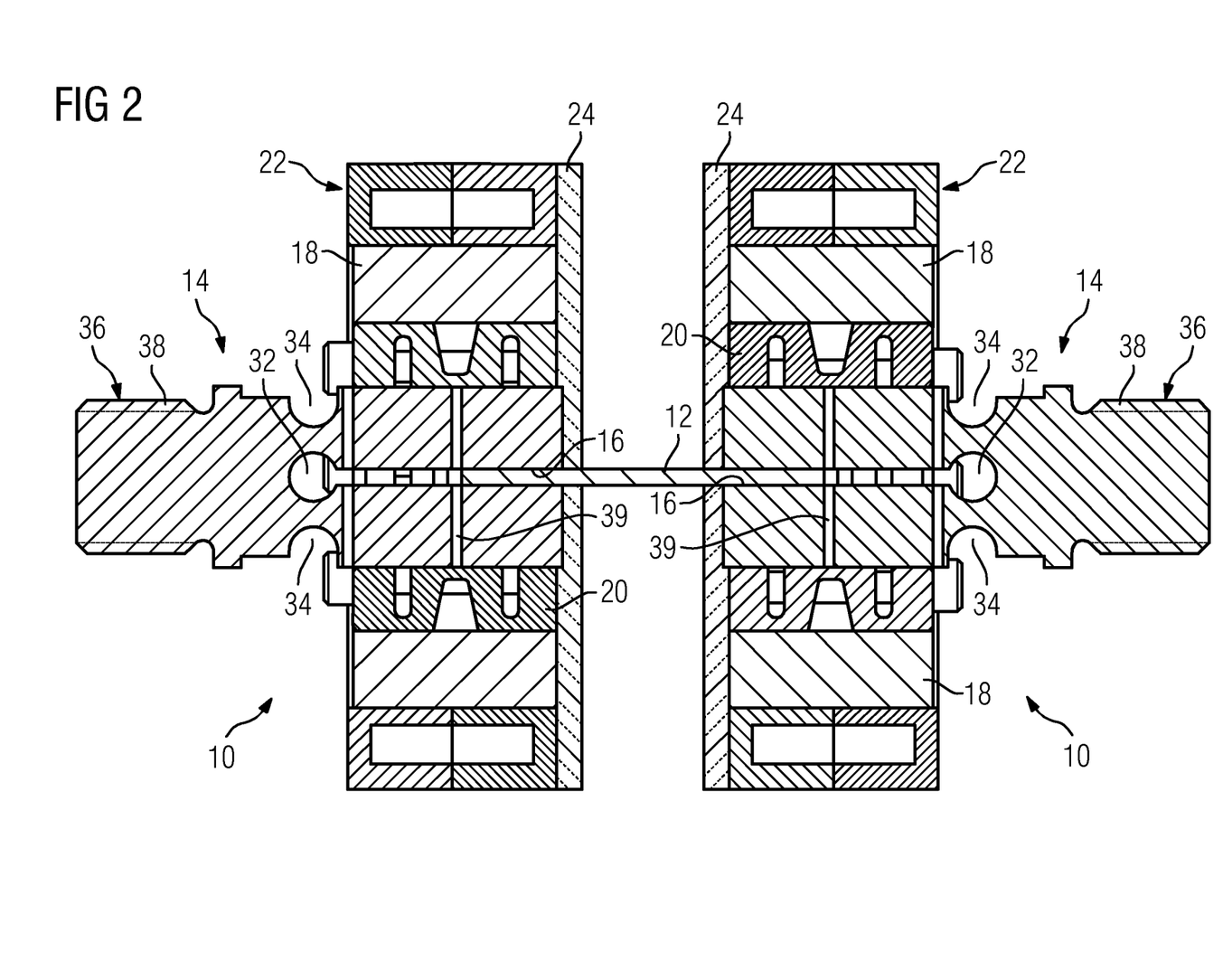
FIG. 2 is a lateral cross-sectional view of the arrangement illustrated in FIG. 1.

FIGS. 1 and 2 show two clamping devices 10 formed according to one embodiment and arranged opposite one another, said clamping devices 10 clamping a flat material test sample 12 between each other. The two clamping devices form a part of a material testing machine, which is used to determine material characteristics. To be more precise, the material testing machine is designed to expose the material test sample held between the clamping devices 10 to different loads, in particular static tensile and/or compressive loads, pulsating loads (R=0 or R=∞) and alternating loads (R=−1). Such material testing machines are known per se, for which reason only the clamping device structure is explained in more detail in the following text.

The clamping devices 10 have identical structures and each comprise, as main components, a substantially cylindrical clamping part 14, from one free end of which a receiving slot 16 for receiving the material test sample 12 extends, a pressure ring 18 which surrounds the clamping part 14 in the region of the receiving slot 16, a pressure sleeve 20 which is provided between the clamping part 14 and the pressure ring 18, a cooling collar 22 which surrounds the pressure ring 18 and through which a cooling fluid can flow, and also a thermal insulator 24 which is provided on the inner end side of each clamping device 10 and is formed in a plate-like manner.

Figure 3:
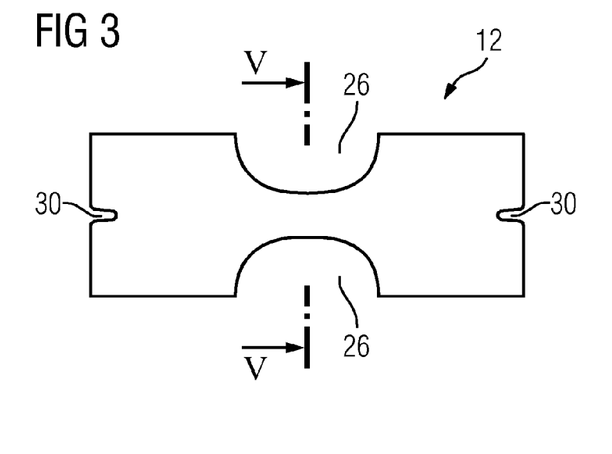
FIG. 3 is a plan view of the material test sample of the arrangement illustrated in FIGS. 1 and 2.
Figure 4:
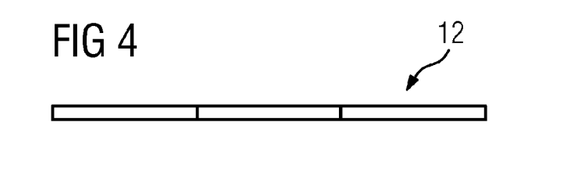
FIG. 4 is a side view of the material test sample.
Figure 5:
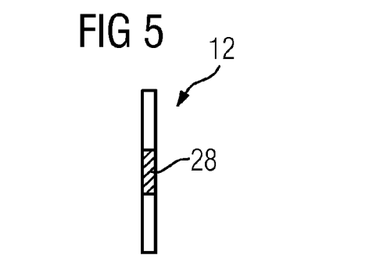
FIG. 5 is a cross-sectional view of the material test sample along the line V-V in FIG. 3.

The material test sample 12, which is illustrated in detail in FIGS. 3 to 5, is a flat, substantially rectangularly formed component, which is produced from a material the material characteristics of which are intended to be determined. Along its mutually opposite longitudinal edges, the material test sample 12 is provided with two cutouts 26 which are arranged centrally and opposite each other, are formed in a rounded manner and define a rectangular test cross section 28. Arranged centrally on the transverse edges of the material sample 12 are mutually opposite slots 30 which are formed in a rounded manner at their slot bases and are used to guide the material test sample 12 during the clamping operation and to center the material test sample 12 in the clamped-in state.

Figure 6:
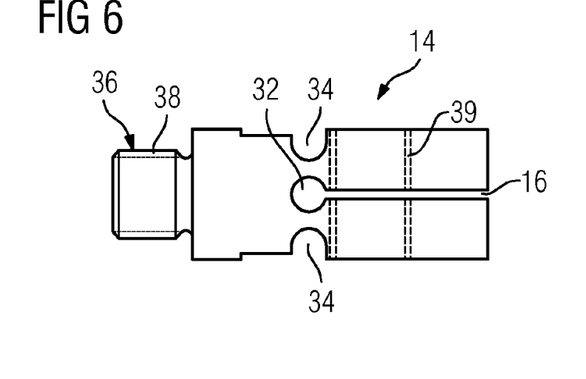
FIG. 6 is a first side view of a clamping part of the arrangement illustrated in FIGS. 1 and 2.
Figure 7:
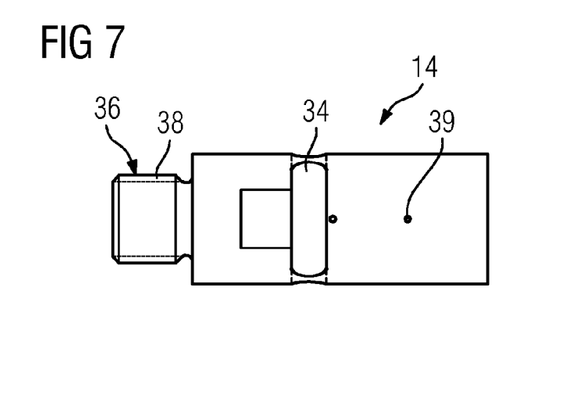
FIG. 7 is a second side view of the clamping part, which has been rotated through 90° with respect to the side view according to FIG. 6.

The clamping part 14 illustrated in detail in FIGS. 6 and 7 is formed in a substantially cylindrical manner. The receiving slot 16, which is used to receive the material test sample 12, extends from one free end or from the end side of the clamping part 14. The receiving slot 16 is widened at its slot base 32 by a bore. The outside diameter of the clamping part 14 is provided in the region of the slot base 32 of the receiving slot 16 with two mutually opposite grooves 34, which are arranged at the same distance from the receiving slot 16 and have a groove base that is semicircular in cross section. At its other free end or in the region of the other end side, the clamping part 14 has a fastening section 36 for fastening the clamping part 14 to the material testing machine. The fastening section 36 is provided with a thread 38 which can be brought into engagement with a correspondingly formed mating thread on the material testing machine. Perpendicularly to the receiving slot 16, there extends a transverse bore 39 which is used to receive an indexing pin (not illustrated in more detail) that interacts with the slot 30 in the material test sample 12 for the purpose of centering.

Figure 8:
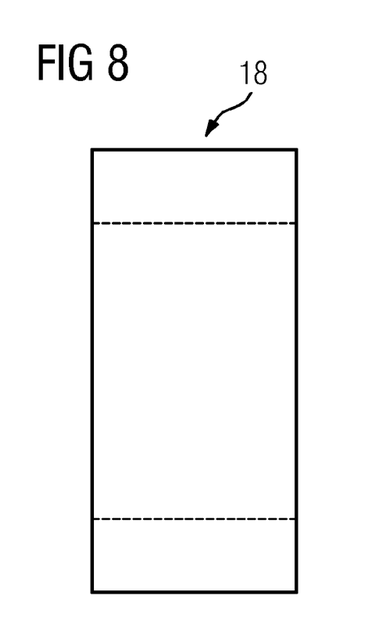
FIG. 8 is a side view of a pressure ring of the arrangement illustrated in FIGS. 1 and 2.
Figure 9:
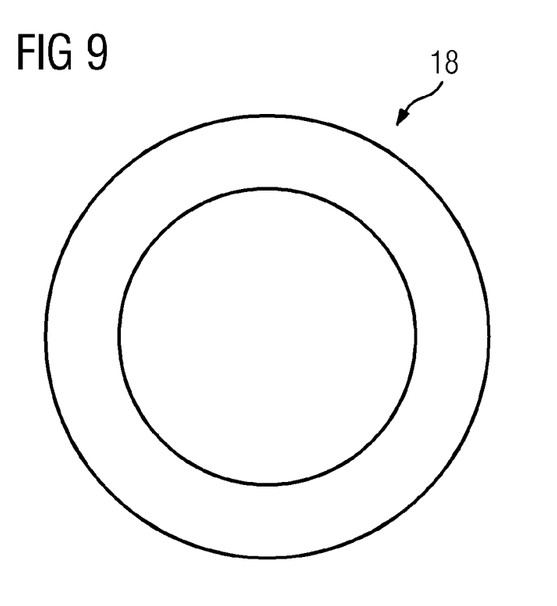
FIG. 9 is a front view of the pressure ring.
Figure 10:
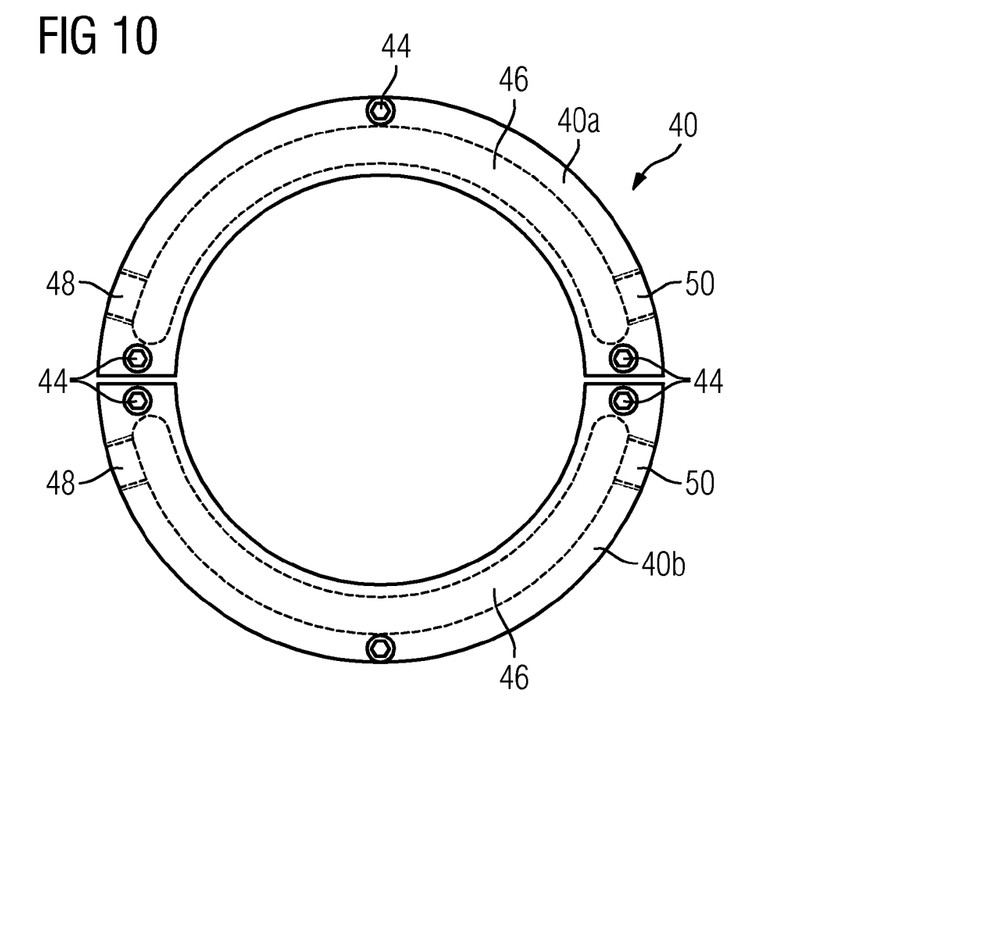
FIG. 10 is a front view of a cooling collar of the arrangement illustrated in FIGS. 1 and 2.
Figure 11:
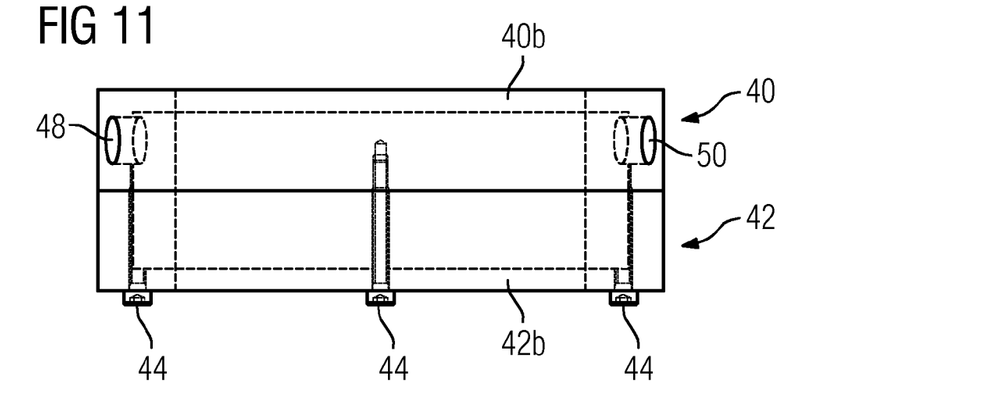
FIG. 11 is a first side view of the cooling collar.
Figure 12:
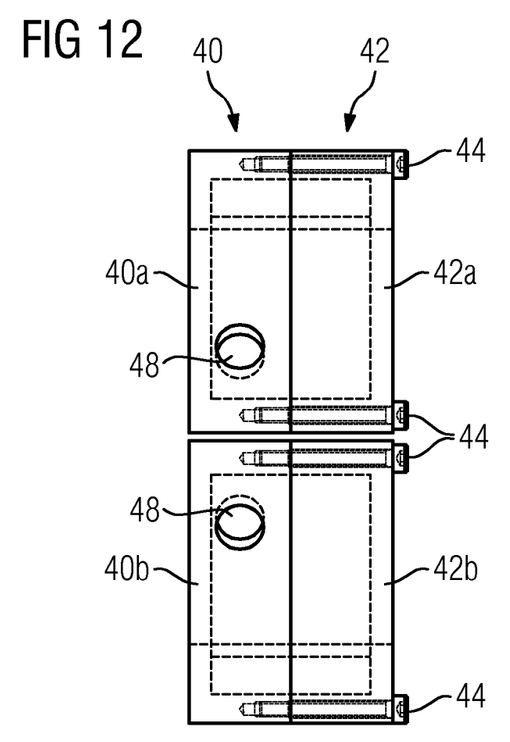
FIG. 12 is a second side view of the cooling collar, which has been rotated through 90° with respect to the side view illustrated in FIG. 11.
Figure 13:
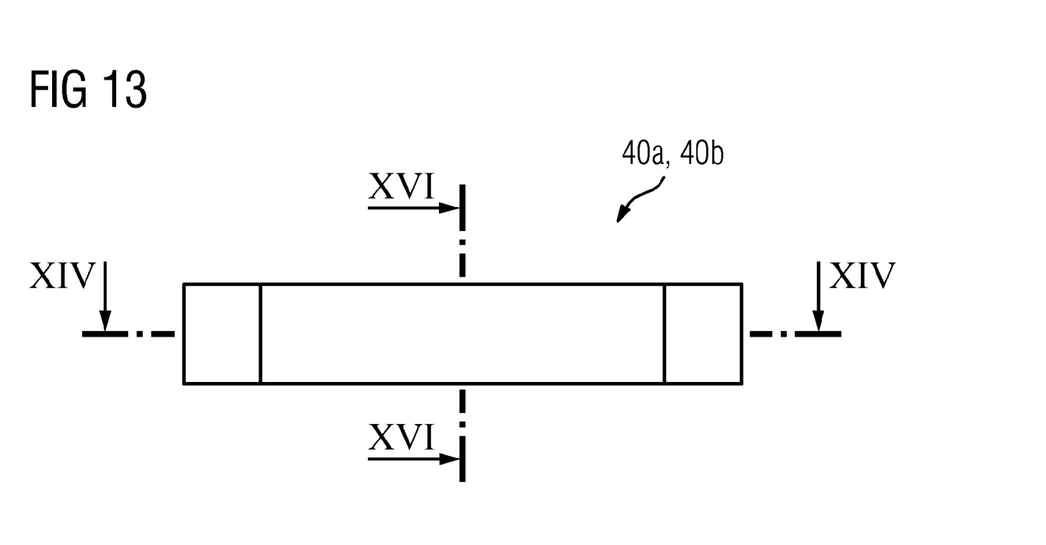
FIG. 13 is a side view of an inner cooling collar half-ring of the cooling collar illustrated in FIGS. 10 to 12.
Figure 14:
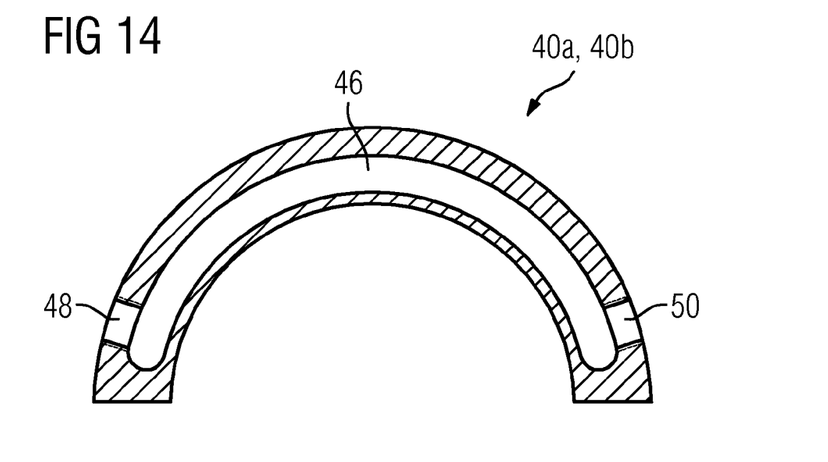
FIG. 14 is a cross-sectional view of the inner cooling collar half-ring along the line XIV-XIV in FIG. 13.
Figure 15:
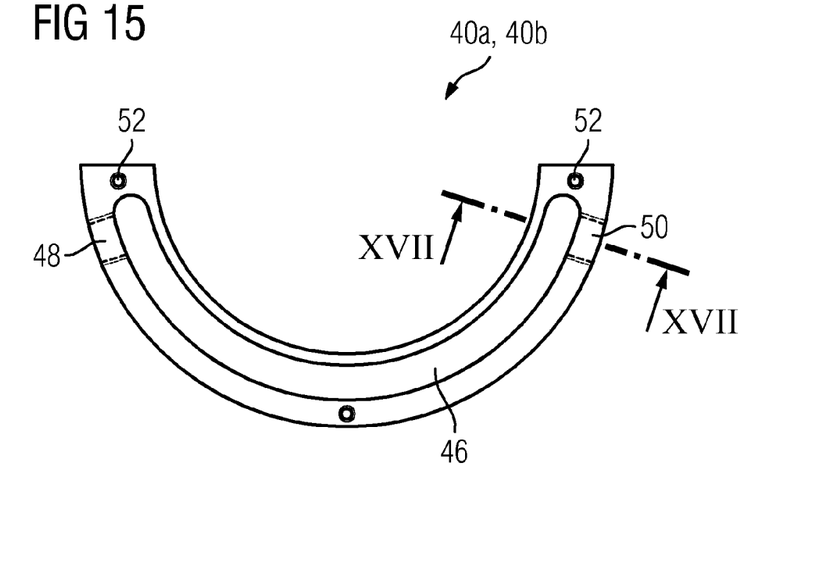
FIG. 15 is a bottom view of the inner cooling collar half-ring.
Figure 16:
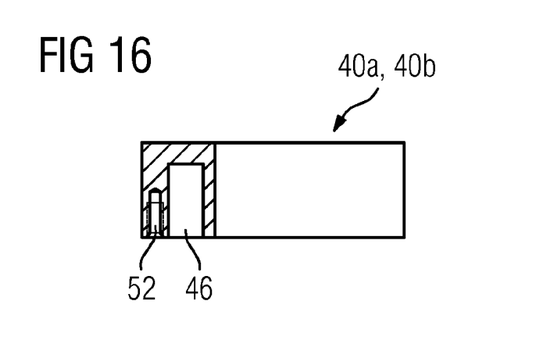
FIG. 16 is a cross-sectional view of the inner cooling collar half-ring along the line XVI-XVI in FIG. 13.
Figure 17:
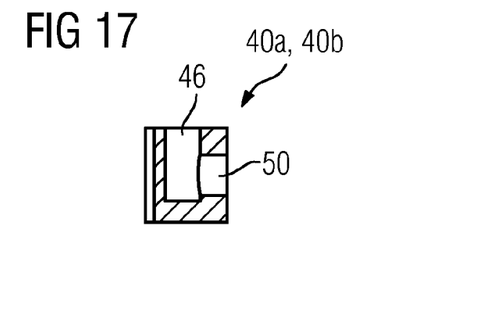
FIG. 17 is a cross-sectional view of the inner cooling collar half-ring along the line XVII-XVII in FIG. 15.
Figure 18:
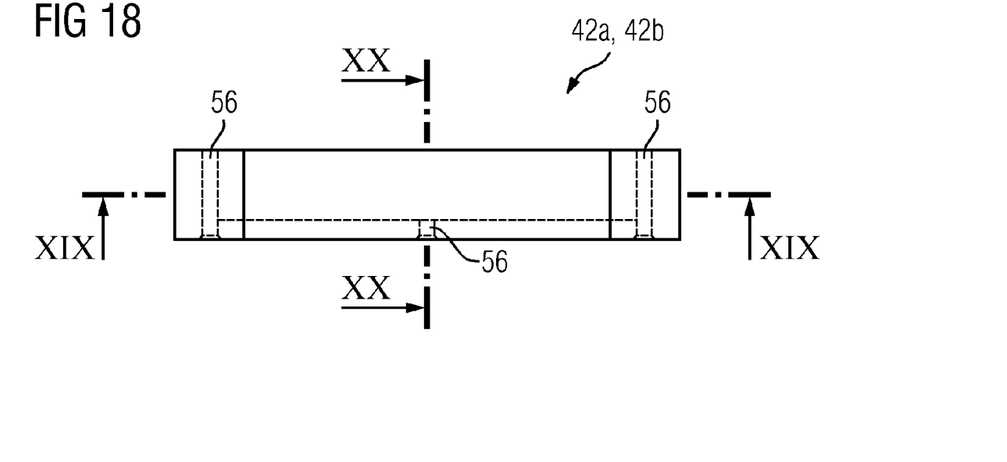
FIG. 18 is a side view of an outer cooling collar half-ring of the cooling collar illustrated in FIGS. 10 to 12.
Figure 19:
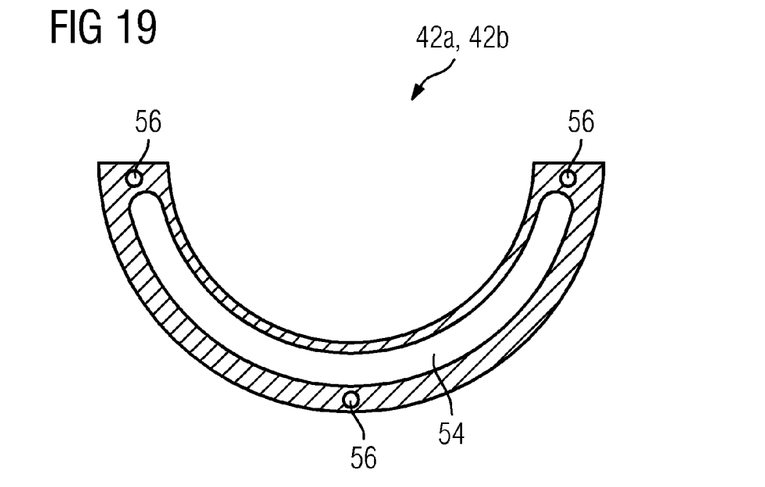
FIG. 19 is a cross-sectional view of the outer cooling collar half-ring along the line XIX-XIX in FIG. 18.
Figure 20:
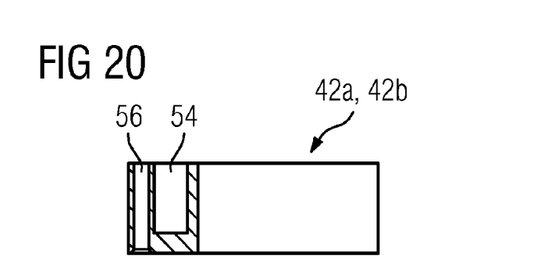
FIG. 20 is a cross-sectional view of the outer cooling collar half-ring along the line XX-XX in FIG. 18.

The pressure ring 18, which is illustrated in detail in FIGS. 8 and 9, is formed as a solid component made of a high-strength material so that it can absorb forces, which act thereon via the pressure sleeve 20, without significant self-deformation.

The cooling collar 22 is illustrated in detail in FIGS. 10 to 20. The cooling collar 22 comprises an inner cooling collar ring 40 and an outer cooling collar ring 42, which are connected together via screws 44. The inner cooling collar ring 40 has two structurally identical inner cooling collar half-rings 40a and 40b, which are each provided with a groove-like cooling-fluid duct 46 that is closed at the two free ends. In the region of its free ends, the cooling-fluid duct 46 is provided on one side with a threaded cooling-fluid inlet bore 48 and on the other side with a threaded cooling-fluid outlet bore 50, it being possible to connect cooling-fluid lines to said threaded bores 48, 50. Accordingly, a coolant can be passed through the cooling-fluid duct 46 from the threaded cooling-fluid inlet bore 48 to the threaded cooling-fluid outlet bore 50. Formed in the inner cooling collar half-ring 40a, 40b are blind threaded holes 52 in which the screws 44 are received when the cooling collar 22 is fitted. The outer cooling collar ring 42, too, comprises two structurally identical cooling collar half-rings 42a, 42b, one of which is illustrated in detail in FIGS. 18 to 20. In an analogous manner to the inner cooling collar half-rings 40a and 40b, the outer cooling collar half-rings 42a, 42b are also provided with a groove-like cooling-fluid duct 54 which is formed in a closed manner at its free ends and the dimensions of which, as seen in cross section, correspond substantially to the dimensions of the cooling-fluid duct 46 of the inner cooling collar half-rings 40a, 40b, see in particular FIG. 19 in this regard. Furthermore, the outer cooling collar half-rings 42a, 42b have through-passage bores 56 for receiving the screws 44, said through-passage bores 56 being arranged congruently with the blind threaded holes 52 in the inner cooling collar half-rings 40a, 40b.

Figure 21:
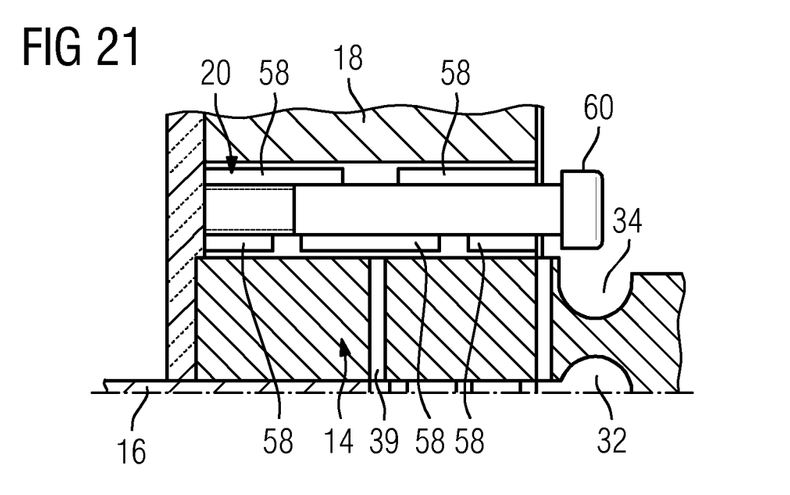
FIG. 21 is a view of a detail from FIG. 2, which schematically shows an illustrated clamping sleeve of the arrangement in the unclamped state.
Figure 22:
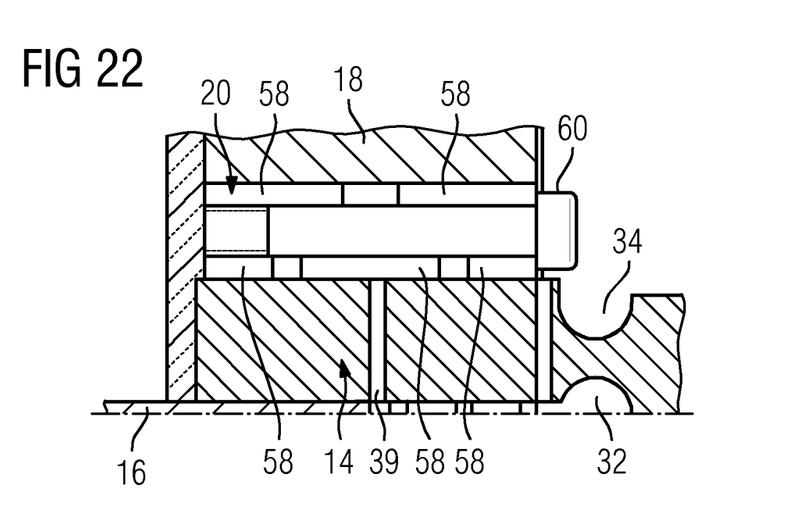
FIG. 22 is a view of the detail from FIG. 2, which schematically shows the clamping sleeve in the clamped state.

The pressure sleeve 20 is a commercially obtainable component which can be obtained as a shaft-hub connecting element (series DSK-DSL) for example from the company Spieth-Maschinenelemente GmbH & Co. KG, Esslingen, Germany. The pressure sleeve 20 is formed and actuable such that, under radial expansion, it connects the clamping part 14 and the pressure ring 18 together and clamps the material test sample 12 held in the receiving slot 16. To be more precise, the pressure sleeve 20, as is illustrated schematically in FIGS. 21 and 22, comprises a plurality of annular clamping elements 58 which can be clamped or released by tightening or loosening clamping screws 60 under radial expansion. If the clamping screws 60 are tightened, as is illustrated in FIG. 22, then a uniform surface pressure is brought about radially via the clamping elements 58 both on the clamping part 14 and on the pressure ring 18. Accordingly, the clamping part 14 and the pressure ring 18 are connected firmly together. At the same time, the clamping part sections that bound the receiving slot 16 from above and below are moved toward each other with the receiving slot 16 narrowing, this being facilitated by the widening of the slot base and also by the grooves 34. Accordingly, the material sample 12 received in the receiving slot 16 is uniformly clamped and centered. In this state, the material sample 12 is held optimally for any loading, in particular for symmetrical alternating tensile and compressive loading. If the clamping screws 60 are loosened again after a material test has been carried out, the receiving slot 16 widens again, as is shown in FIG. 21, such that the material test sample 12 can be removed again without problems. Subsequently, a new material test sample 12 can be received in the clamping devices 10.

We claim:

1. A clamping device for clamping a flat material test sample while a material test is carried out, comprising:
   a substantially cylindrical clamping part, from the free end of which there extends a receiving slot for receiving the material test sample;
   a pressure ring concentrically surrounding the clamping part in the region of the receiving slot; and
   a pressure sleeve provided between the clamping part and the pressure ring such that the pressure sleeve is concentric with the clamping part and the pressure ring in the region of the receiving slot, the pressure sleeve is formed and actuable such that, under radial expansion, it connects the clamping part and the pressure ring together and clamps the material test sample held in the receiving slot.

2. The clamping device as claimed in claim 1, wherein the receiving slot is widened at a slot base, and wherein the widening has a circular cross section.

3. The clamping device as claimed in claim 2, wherein the outside diameter of the clamping part has a groove in the region of the slot base of the receiving slot.

4. The clamping device as claimed in claim 3, wherein the outside diameter of the clamping part has two grooves located opposite one another, which are arranged at the same distance from the receiving slot.

5. The clamping device as claimed in claim 1, wherein the clamping part has at its other free end a fastening section for arranging the clamping part on a material testing machine.

6. The clamping device as claimed in claim 5, wherein the fastening section of the clamping part is provided with a thread which is brought into engagement with a correspondingly formed mating thread on the material testing machine.

7. The clamping device as claimed in claim 1, wherein the pressure ring is in the form of a solid component.

8. The clamping device as claimed in claim 1, wherein there is provided a cooling collar through which a coolant flows and which surrounds the pressure ring.

9. The clamping device as claimed in claim 1, wherein a thermal insulator is provided on an end side of the clamping device, the thermal insulator is formed in a plate-like manner.

10. The clamping device as claimed in claim 1, wherein a thermal insulator is provided on an end side of the clamping device, the thermal insulator is produced from ceramic material.

11. A material testing machine, comprising:
    two clamping devices, each clamping device, comprising:
       a substantially cylindrical clamping part, from the free end of which there extends a receiving slot for receiving the material test sample;
       a pressure ring concentrically surrounding the clamping part in the region of the receiving slot; and
       a pressure sleeve provided between the clamping part and the pressure ring such that the pressure sleeve is concentric with the clamping part and the pressure ring in the region of the receiving slot, the pressure sleeve is formed and actuable such that, under radial expansion, it connects the clamping part and the pressure ring together and clamps the material test sample held in the receiving slot,
    wherein the two clamping devices are arranged opposite one another such that the free ends of a flat material test sample are receivable in their receiving slots and the material test sample may be clamped.

\* \* \* \* \*